(12) United States Patent
Roberson et al.

(10) Patent No.: US 8,815,603 B2
(45) Date of Patent: Aug. 26, 2014

(54) INCORPORATION OF CHEMOCHROMIC PIGMENT INTO A VARIETY OF ARTICLES AS AN INDICATOR FOR THE PRESENCE OF HYPERGOLIC FUELS

(75) Inventors: Luke B. Roberson, Titusville, FL (US); Robert W. DeVor, Titusville, FL (US); Janine E. Captain, Titusville, FL (US); Edgardo Santiago-Maldonado, Beavercreek, OH (US)

(73) Assignee: The United States of America as Represented by the Administrator of the National Aeronautics and Space Administration, Washington, DC (US)

( * ) Notice: Subject to any disclaimer, the term of this patent is extended or adjusted under 35 U.S.C. 154(b) by 43 days.

(21) Appl. No.: 13/546,880

(22) Filed: Jul. 11, 2012

(65) Prior Publication Data

US 2013/0017617 A1    Jan. 17, 2013

Related U.S. Application Data

(60) Provisional application No. 61/506,219, filed on Jul. 11, 2011.

(51) Int. Cl.
*G01N 21/78* (2006.01)
*G01N 33/22* (2006.01)

(52) U.S. Cl.
USPC ........... 436/106; 436/164; 436/166; 436/181; 422/400; 422/425; 422/86; 422/88

(58) Field of Classification Search
USPC ........... 436/56, 73, 79, 80, 84, 106, 124, 127, 436/164, 166, 169, 181; 422/400, 408, 418, 422/419, 420, 425, 83, 86, 87, 88; 423/463, 423/599
See application file for complete search history.

(56) References Cited

U.S. PATENT DOCUMENTS

| | | |
|---|---|---|
| 5,398,153 A | 3/1995 | Clough |
| 5,849,073 A | 12/1998 | Sakamoto |
| 6,015,715 A | 1/2000 | Kirschner |
| 6,172,120 B1 | 1/2001 | Smith |
| 6,895,805 B2 | 5/2005 | Hoagland |
| 2004/0050143 A1 | 3/2004 | Hoagland |
| 2005/0092761 A1 | 5/2005 | Marganski |
| 2005/0159497 A1 | 7/2005 | Gauthier |
| 2006/0127543 A1* | 6/2006 | Klein et al. .................. 426/263 |
| 2007/0125153 A1 | 6/2007 | Visel |
| 2007/0224081 A1 | 9/2007 | Bokerman |
| 2009/0053104 A1* | 2/2009 | Buttner et al. .................. 422/55 |
| 2009/0062424 A1* | 3/2009 | Hein ............................. 523/135 |
| 2011/0171066 A1 | 7/2011 | Captain |

* cited by examiner

*Primary Examiner* — Maureen Wallenhorst
(74) *Attorney, Agent, or Firm* — Michelle L. Ford; Jennifer P. Yancy

(57) ABSTRACT

A chemochromic indicator is provided that includes a hypergolic fuel sensing chemochromic pigment that change from a first color to a second color in the presence of a hypergolic fuel. In a first embodiment, a chemochromic indicator is provided for detecting the presence of a hypergolic fuel such that the irreversible hypergolic fuel sensing chemochromic pigment includes potassium tetrachloroaurate ($KAuCl_4$). There are several types of chemochromic indicators, for example, the article used to form the chemochromic indicators include, but are not limited to, wipe materials, silicone/TEFLON tape, manufactured parts, fabrics, extruded parts, and paints.

12 Claims, 4 Drawing Sheets

XPS spectra for gold and KAuCl$_4$

XPS spectra for 5% $KAuCl_4$ on silica and 5% $KAuCl_4$ on silica exposed to hypergols

INCORPORATION OF CHEMOCHROMIC PIGMENT INTO A VARIETY OF ARTICLES AS AN INDICATOR FOR THE PRESENCE OF HYPERGOLIC FUELS

CROSS REFERENCE TO RELATED APPLICATION

This application claims the benefit, under 35 U.S.C. 119(e), of U.S. Provisional Patent Application Ser. No. 61/506,219, filed on Jul. 11, 2011, the contents of which are incorporated herein by reference.

ORIGIN OF THE INVENTION

The invention described herein was in the performance of work under a NASA contract and made by employees of the United States Government and is subject to the provisions of Public Law 96-517 (35 U.S.C. §202) and may be manufactured and used by or for the Government for governmental purposes without the payment of any royalties thereon or therefor. In accordance with 35 U.S.C. §202, the contractor elected not to retain title.

TECHNICAL FIELD OF THE INVENTION

The present invention is directed to a chemochromic indicator and process for detecting hypergolic fuels that includes the incorporation of a chemochromic pigment into a variety of articles.

BACKGROUND OF THE INVENTION

Hydrazine and other derivative hypergolic fuels are used as rocket propellants. The auxiliary power units on the Space Shuttle Orbiter used monomethylhydrazine (MMH) to provide power through hydrogen generation for electrolysis. The orbiters also used hydrazine derivatives in the Orbiter Maneuvering System (OMS) pods to orient the shuttle in space. Satellites, space planes, and other rocket payloads also consume hydrazine derivatives as fuel. Commercially, hydrazine is used as a polymerization catalyst, a blowing agent, an oxygen scavenger, and a reducing agent. Hydrazine is highly toxic, highly flammable, and even at very low concentrations can strongly irritate the nose, eyes, and throat. Dizziness, nausea, and death can result from the inhalation of hydrazine. Hydrazine gas is colorless making it difficult to visually detect; however, at 3-4 ppm, the odor of hydrazine is detectable by the human nose. Yet the acceptable concentration limits for human exposure are 4 ppm over one hour, 0.9 ppm from 1 day to 30 days, and 0.15 ppm for 6 months, meaning that once someone detects hydrazine or its derivatives via smell, the person has already been exposed to excessive, harmful concentrations.

Hazardous gas detection is critical for the safety of personnel and equipment. Current means for monitoring hypergolic fuel leakage is inadequate to accurately and quickly determine leaks, allowing personnel to be exposed to dangerous concentrations of hypergolic vapors. Because the acceptable exposure limits are extremely low for hydrazine and other derivative hypergolic fuels, a chemochromic detecting device would provide an immediate visual warning to the presence of hydrazine and other derivative hypergolic fuels, thus protecting personnel from dangerous chemical vapor ingestion.

Incorporated into a suitable product matrix, a chemochromic pigment adapted to change color in the presence of hypergolic vapors would provide a means for notifying personnel of their potential exposure to hypergolic leakage. The ability to manufacture Personnel Protective Equipment (PPE) having the capability to detect miniscule levels (up to ppb) of hydrazine and rapidly respond chemochromically in the presence of toxic chemicals would be of great use to personnel working with these chemicals.

As will be discussed in detail hereafter, the present invention is directed to a process for cost effectively synthesizing a chemochromic pigment that indicates the presence of hypergolic fuels, such as hydrazine, and incorporating said chemochromic pigments into a variety of articles including, but not limited to, tapes, paints, and textiles.

SUMMARY OF THE INVENTION

The present invention is directed to chemochromic indicators that include hypergolic fuel sensing chemochromic pigments that change from a first color to a second color in the presence of a hypergolic fuel in either gas or liquid form. The incorporation of the hypergolic fuel sensing chemochromic pigments into articles for the formation of the chemochromic indicators provides increased safety through a quick and easily understood visual detection system for the presence of hypergolic fuels. The chemochromic indicator may be incorporated into a worker's personnel protective equipment (PPE) or placed in close proximity to a potential leakage source.

A chemochromic indicator is provided for detecting the presence of a hypergolic fuel. The chemochromic indicator includes a hypergolic fuel sensing pigment which is capable of an oxidation-reduction reaction with hypergolic fuels wherein said hypergolic fuel sensing chemochromic pigment undergoes an irreversible color change. The hypergolic fuel sensing pigment may be provided alone or incorporated onto an inert substrate. In a first embodiment, the chemochromic indicator includes an irreversible hypergolic fuel sensing chemochromic pigment such as potassium tetrachloroaurate ($KAuCl_4$) or potassium permanganate ($KMnO_4$). In one embodiment, the hypergolic fuel sensing chemochromic pigment can be used alone to detect hydrazine or its derivatives, or it can also be deposited onto an inert substrate. The hypergolic fuel is detected by exposing the chemochromic indicator to a hypergolic fuel, such that the hypergolic fuel sensing chemochromic pigment changes from a first color to a second color indicating the presence of the hypergolic fuel, gas, or liquid.

For example, the color change may be such that the chemochromic indicator including a potassium tetrachloroaurate (III) ($KAuCl_4$) salt changes from a first color of yellow to a second color of black when exposed to the hypergolic fuel. When the $KAuCl_4$ salt reacts with the vapors of a hypergolic fuel, such as hydrazine and/or monomethylhydrazine (MMH), a change in color occurs from yellow to black. This color change is indicative of an oxidation-reduction reaction in which the gold (III) is reduced to the zero-valent state, and the hydrazine is oxidized. The color change is the appearance of the reduced gold particles, which appears dark purple to black in color when gold nanoparticles are formed from the reduction of the $KAuCl_4$ salt. The chemochromic indicator may be in the form of a tape incorporating the $KAuCl_4$ salt which is utilized where a suspected leak of hypergolic fuel, such as hydrazine or MMH, would occur to give an early indication of the presence of the harmful compound.

In a second embodiment, the chemochromic indicators in the first embodiment are combined into a host material and manufactured into an article for detection. The host material can be any material capable of incorporating the hypergolic fuel sensing chemochromic pigment and is chemically compatible with hypergolic fuels. For example, one may incorporate the hypergolic fuel sensing chemochromic pigments into a tape which can be applied to valves and flanges for leak detection. The hypergolic fuel sensing chemochromic pigment may be incorporated into a standard paint base such as urethanes or epoxies for painting hypergolic fuel containment vessels. In addition, the hypergolic fuel sensing chemochromic pigment could be blended through melt mixing, extrusion, molding, or similar manufacture techniques to manufacture parts containing the hypergolic fuel sensing chemochromic pigment; or they could be incorporated into textiles and woven into PPE for containment suits or gloves. In each case, the chemochromic indicator changes from a first color to a second color demonstrating the presence of hypergolic fuels.

BRIEF DESCRIPTION OF THE DRAWINGS

The features and advantages of the present invention will become apparent from the following detailed description of a preferred embodiment thereof, taken in conjunction with the accompanying drawings, in which.

DETAILED DESCRIPTION OF THE INVENTION

Figure 1A:
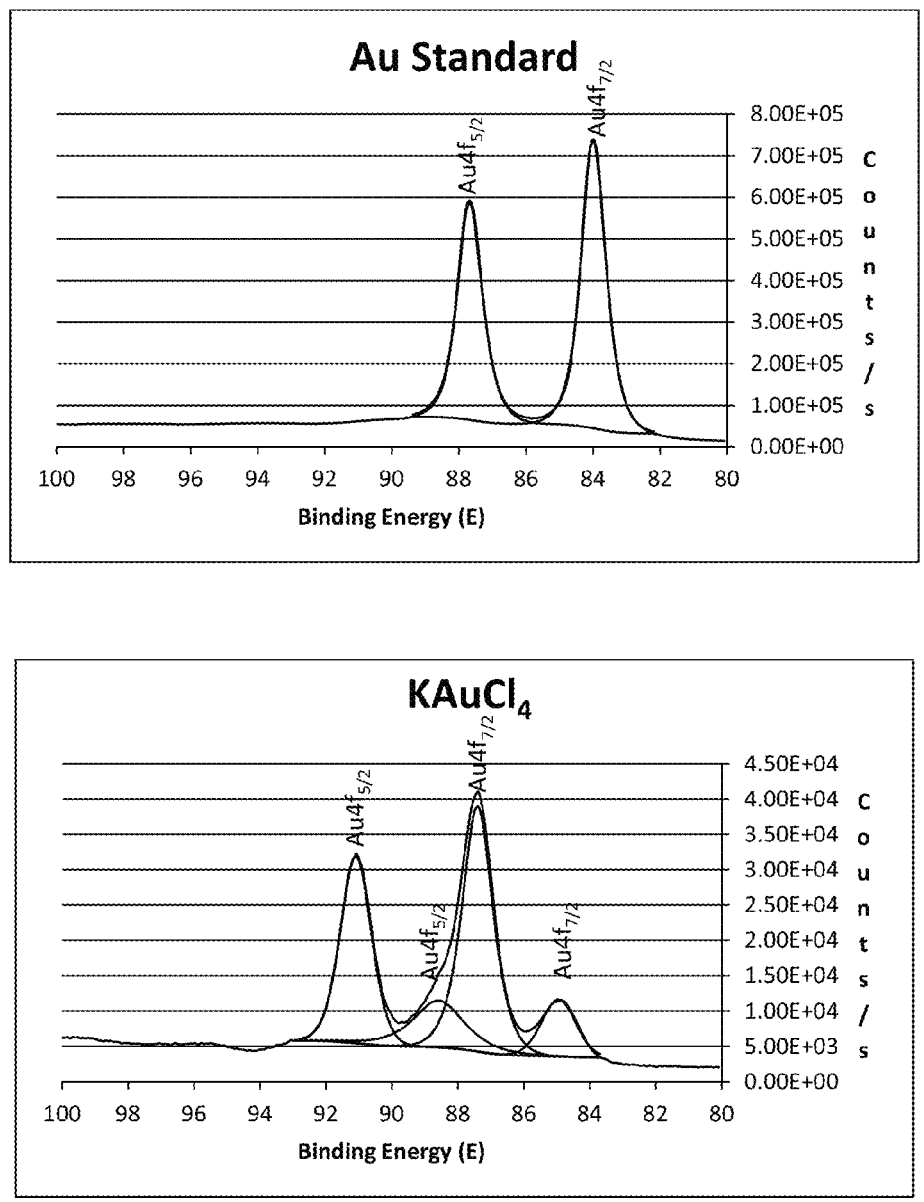
FIGS. 1A and 1B provide graphs showing the XPS spectra for gold, $KAuCl_4$, 5% $KAuCl_4$ on silica, and 5% $KAuCl_4$ on silica exposed to hypergolic fuels.

The present invention is directed to chemochromic indicators that include hypergolic fuel sensing chemochromic pigments that change from a first color to a second color in the presence of a hypergolic fuel. The hypergolic fuel sensing chemochromic pigment is capable of an oxidation-reduction reaction with hypergolic fuels wherein said hypergolic fuel sensing chemochromic pigment undergoes an irreversible color change. There are several types of chemochromic indicators, each of which may be useful in a variety of sensing application. For example, the article used to form the chemochromic indicators include, but are not limited to, wipe materials, silicone/TEFLON tape, manufactured parts, fabrics, extruded parts, and paints. The incorporation of the hypergolic fuel sensing chemochromic pigments into articles for the formation of the chemochromic indicators allows for an increase in safety, as this would provide a quick and easily understood detection system for the presence of hypergolic fuels. The chemochromic indicator may be incorporated into a worker's personnel protective equipment (PPE) or placed in close proximity to a potential leakage source. For uses at a launch site where electrostatic discharge must be controlled, the article (such as a tape) incorporating the hypergolic fuel sensing chemochromic pigment must pass a flammability and electrostatic discharge test. Additionally, it is preferred that the article including the hypergolic fuel sensing chemochromic pigment be protected from ultraviolet (UV) light which could adversely affect the reactivity of the hypergolic fuel sensing chemochromic pigment. Commercially available anti-electrostatic coatings and UV protectant surface treatments may be used on the article including the hypergolic fuel sensing chemochromic pigment to meet such needs. The antistatic coating and UV protectant may be applied to a surface of the article.

In a first embodiment, an irreversible hypergolic fuel sensing chemochromic pigment is incorporated into an article such that a color change occurs when the article is exposed to the hypergolic fuel. The irreversible hypergolic fuel sensing chemochromic pigment includes potassium tetrachloroaurate (III) ($KAuCl_4$) that is initially yellow in color. When the $KAuCl_4$ salt reacts with the vapors of a hypergolic fuel, such as hydrazine and/or monomethylhydrazine (MMH), a change in color occurs from yellow to black. This color change is indicative of an oxidation-reduction reaction in which the gold (III) is reduced to the zero-valent state, and the hydrazine is oxidized. The color change is the appearance of the reduced gold particles, which appears dark purple to black in color when gold nanoparticles are formed from the reduction of the gold salt.

In another embodiment, the hypergolic fuel sensing chemochromic pigment contains a counter ion which includes, but is not limited to, hydrogen, any group 1 or group 2 alkali metal, sulfur dioxide ($SO_2$), ammonium ($NH_4$), a transition metal, or a lanthanide metal. The active metal center of the compound could be any transition lanthanide or actinide metal. Such as, manganese, iron, copper, zinc, or similar metals that can process through a +3 to 0 oxidation transition or a +2 to 0 oxidation transition upon exposure to hypergols. Additionally, the chemochromic pigment contains any ligand which includes, but is not limited to, chlorine, fluorine, iodine, bromine, or oxygen.

In yet another embodiment, the hypergolic fuel sensing chemochromic pigment may be plated onto an inert spherical particle substrate forming a hypergolic fuel sensing substrate that is then incorporated into the article. The substrate increases the surface area of the chemochromic pigment, thereby increasing the change in color response as well as decreasing the cost of pigment synthesis. The substrate could be any inert or reactive chemical substance that doesn't proceed through an oxidative-reductive reaction. Particle size of the substrate can vary based on specific application needs, but typical particle sizes are in the 50-200 micron diameter. Preferably, the inert substrate is a ceramic oxide which includes, but is not limited to, titanium dioxide ($TiO_2$), silica, zirconia and alumina. During laboratory experiments, the color change of the $KAuCl_4$ salt on an inert substrate including silica was most pronounced. For example, the irreversible hypergolic fuel sensing chemochromic pigment was prepared by depositing a $KAuCl_4$ salt pigment onto an inert substrate, for example, silica gel, in various mesh sizes. The deposition of the $KAuCl_4$ salt pigment was achieved by adding an appropriate amount of silica gel and placing it in a round bottom flask and then an appropriate amount of $KAuCl_4$ salt solution (dissolved into ethanol or other appropriate solvent) was also added to the round bottom flask. The round bottom flask was subjected to rotary evaporation until all of the solvent was removed and the remaining solid was completely dry. Rotary evaporation allows for easy and uniform (although uniformity is not required) distribution of varying batch sizes, thereby allowing for up-scaling as required. Although silica gel is preferably utilized as the inert substrate, other possible substrates such as titanium dioxide and alumina are considered within the scope of the present invention. This deposition process allows for a much more cost-effective use of the $KAuCl_4$ salt pigment, as the active component is only on the surface of the inert substrate. This allows a much smaller amount of $KAuCl_4$ salt to be used in various sensor applications, while still providing a more than adequate chemochromic response to hypergolic fuels. At this point, the prepared hypergolic fuel sensing substrate with the irreversible hypergolic fuel sensing chemochromic pigment was incorporated into a variety of different articles for use as a chemochromic indicator. The inert substrate does not interfere or affect the oxidation reduction reaction which occurs between the $KAuCl_4$ salt and the hypergolic fuel, i.e. the reaction causing the chemochromic change from yellow to purple/black when exposed to hypergolic fuel vapors.

In another embodiment, a host material incorporating any of the previous embodiments could be manufactured into an article and utilized where a suspected leak of hypergolic fuel, such as hydrazine or MMH, would occur to give an early indication of the presence of the harmful compound. The irreversible hypergolic fuel sensing chemochromic pigment may be incorporated into a variety of host materials to form articles including, but not limited, to tape, manufactured parts, fabrics, extruded parts, and paints. In another embodiment, the irreversible hypergolic fuel sensing chemochromic pigment is incorporated into a Dow Corning 3145 room temperature vulcanized (RTV) material. After incorporation of the hypergolic fuel sensing chemochromic pigment into the clear RTV, the silicone became yellow, was spread out into thin sheets, and cut into thin strands of tape. The tape was then exposed to hydrazine, where it immediately changed color to black. In another embodiment, the hypergolic fuel sensing chemochromic pigment was incorporated into polytetrafluoroethylene (PTFE) and extruded into a tape format. The tape was an off-white color, but when exposed to hydrazine, changed color to black. In other embodiments, the hypergolic fuel sensing chemochromic pigment was mixed into a clear polymer resin and extruded into melt-spun fibers to generate fabrics. In another embodiment, the hypergolic fuel sensing chemochromic pigments were mixed with a clear polymer material and manufactured into a host material, such as a storage vessel or tubing.

The following non-limiting examples set forth below illustrate specific examples of the chemochromic indicators and hypergolic fuel sensing chemochromic pigments in accordance with embodiments of the invention. However, it is understood that one of ordinary skill in the art would understand how to adapt these examples without departing from the scope of the invention.

EXAMPLES

Hypergolic Fuel Sensing Chemochromic Pigment

An irreversible hypergolic fuel sensing chemochromic pigment (also referred to herein as "a hypergolic pigment") including $KAuCl_4$ chemically reacts with hydrazine and MMH to produce a color change. The gold (III) is reduced to the zero-valent state while the hydrazine or MMH is oxidized in this oxidation-reduction reaction. An initial hypergolic pigment-containing substrate was prepared by simple evaporative techniques in which the $KAuCl_4$ salt was dissolved in ethanol and mixed with several different inert substrate materials including silicon dioxide ($SiO_2$), alumina ($Al_2O_3$), and titanium dioxide ($TiO_2$) at a 1% by weight loading. The solvent was allowed to evaporate while the solution stirred over a period of several hours. Initial problems with this method included uneven distribution of the $KAuCl_4$ pigment onto the substrate as the solvent evaporated, although initial preliminary tests with hydrazine did show rapid color changes on the dry product. A more effective preparation technique was necessary to evenly distribute the hypergolic pigment onto the substrate surface, and this was produced through the use of a rotary evaporator. A hypergolic pigment-containing substrate was prepared with $KAuCl_4$ as either 1% or 5% by weight with the remaining weight as the substrate. The ethanol was evaporated using a Buchi EL 131 Rotovapor. The water bath was set at approximately 70° C. and vacuum was applied to the system. The end result was a hypergolic pigment-containing substrate with hypergolic pigment evenly distributed on the substrate surface, giving a uniform yellow color for all three substrate materials tested. The three hypergolic pigment-containing substrate materials (at 1% and 5% loadings) were exposed to a mixture of MMH and hydrazine vapors at a concentration of approximately 2500 ppm for 1 minute at 300 sccm. Prior to exposure to MMH and hydrazine, the hypergolic pigment was yellow in color. After exposure, the hypergolic pigment turned purplish black in color, due to the formation of gold nanoparticles. The $KAuCl_4$ salt on $TiO_2$ showed the least dramatic color change, while the $KAuCl_4$ salt on $SiO_2$ showed the best color change.

Additionally, a 10% $KAuCl_4$ salt on silica loading was tested to determine if higher substrate loadings could produce a more vivid color change. Unfortunately, while the initial color of the unexposed hypergolic pigment was a brighter yellow, the final color of the exposed hypergolic pigment remained the same.

A sample of the $KAuCl_4$ salt deposited on the silica was placed in the oven at 108° C. for 5 days and maintained its yellow color. The hypergolic pigment was stable under 108° C. heating conditions.

In order to better understand the chemistry of the reaction, x-ray photoelectron spectroscopy (XPS) analysis was conducted. The $Au4f_{7/2}$ and $Au4f_{5/2}$ peaks for bulk Au(0) were reported as 84.0 and 87.67 eV, respectively, in the literature. The binding energy for $Au4f_{7/2}$ for Au(I) has been reported as 84.5 eV. The resolution of Au(0) and Au(I) peaks at $Au4f_{7/2}$ was often not discernible. The binding energy of Au (III) in the compound $NaAuCl_4$ was determined as 87.10 eV. Other studies in the literature showed shifts in the binding energy for gold when comparing bulk gold to gold nanoparticles plated on graphite. Since the $KAuCl_4$ was deposited on silica when preparing the hypergolic pigment-containing substrate, the possibility existed for shifting of the binding energies associated with the gold, i.e. the measured binding energies of metallic gold and gold in $KAuCl_4$ on silica could deviate from measured binding energies of bulk metallic gold and bulk $KAuCl_4$. From the literature, when gold was in its bulk state, the difference between the binding energy of Au(I) and Au(0) for $Au4f_{7/2}$ was 0.5 eV, and the difference between Au(III) and Au(0) was 3.1 eV. Table 1 shows the results of XPS data collected on the hypergolic pigment. A pure gold film standard was used to calibrate the spectrometer. Several samples were analyzed including the bulk $KAuCl_4$ salt, the $KAuCl_4$ salt in a 1% and 5% load on silica, and the $KAuCl_4$ salt in a 1% and 5% load on silica after exposure by hypergolic vapors. The $Au4f_{7/2}$ and $Au4f_{5/2}$ peaks were determined to be at 84.00 and 87.68 eV for the gold standard, which was very close to the literature values. The Au(III) binding energy for $Au4f_{7/2}$ in the pure salt of $KAuCl_4$ was 87.18 eV, which was close to the literature value for Au(III) in $NaAuCl_4$, which was 87.10 eV. The binding energy at 84.72 for the pure $KAuCl_4$ salt was attributed to Au(I), since Au(I) was seen at 84.5 eV in the literature in a different compound. Since the gold $KAuCl_4$ salt was a bulk sample, no binding energy shifts were expected. Therefore, if the sample contained appreciable amounts of Au(0), the binding energy would be expected around 84.0 eV. The binding energy for $Au4f_{7/2}$ for the unexposed hypergolic pigment at a 1% load of $KAuCl_4$ salt was 83.93 eV. After exposure, the binding energy was 83.34 eV. The difference in energy between the unexposed and exposed 1% $KAuCl_4$ salt hypergolic pigment was 0.59 eV. Therefore, even though the binding energy for the 1% $KAuCl_4$ on silica sample was close to the binding energy of pure gold in its metallic state, the actual valence state was more likely Au(I), prior to exposure, and Au(0) after exposure. The 1% load of KAuCl$_4$ on silica did not discern any Au(III) from the XPS analysis.

TABLE 1

Binding energy results from XPS analysis of hypergol sensing materials.

| Sample | Valence state of gold | Peak 1, Binding Energy, eV, Au4f$_{7/2}$ | Peak 2, Binding Energy, eV, Au4f$_{5/2}$ |
|---|---|---|---|
| Gold Metal | Au(0) | 84.00 | 87.68 |
| Gold Salt, KAuCl$_4$ | Au(I) | 84.72 | 88.27 |
| Gold Salt, KAuCl$_4$ | Au(III) | 87.18 | 90.80 |
| 1% KAuCl$_4$ on Silica | Au(I) | 83.93 | 87.60 |
| 1% KAuCl$_4$ on Silica exposed to Hypergols | Au(0) | 83.34 | 87.01 |
| 5% KAuCl$_4$ on Silica | Au(I) | 84.43 | 88.01 |
| 5% KAuCl$_4$ on Silica | Au(III) | 87.82 | 90.89 |
| 5% KAuCl$_4$ on Silica exposed to Hypergols | Au(0) | 83.70 | 87.45 |
| 5% KAuCl$_4$ on Silica exposed to Hypergols (large clumps) | Au(0) | 83.97 | 87.64 |

The shifts in binding energies for the 5% KAuCl$_4$ were not easily explained. When comparing the binding energy for the Au(I) peak to the bulk sample, it shifted −0.20 eV. However, when comparing the Au(III) peak of the 5% KAuCl$_4$ on silica to the bulk sample, the binding energy increased by 0.64 eV. Several factors have been suggested that contribute to shifts in binding energies including valence electron density, crystal field potential, work function, and relaxation energy, as well as particle size and charge transfer. Regardless of the cause, clearly the electronic nature of the binding energy of gold was influenced by the differences in the samples.

Figure 1B:
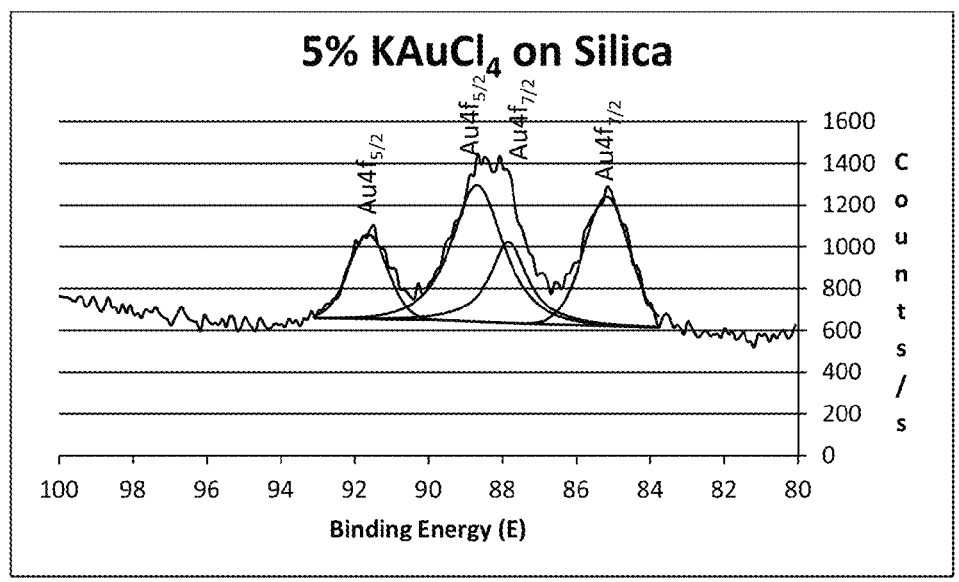
Figure 1B:
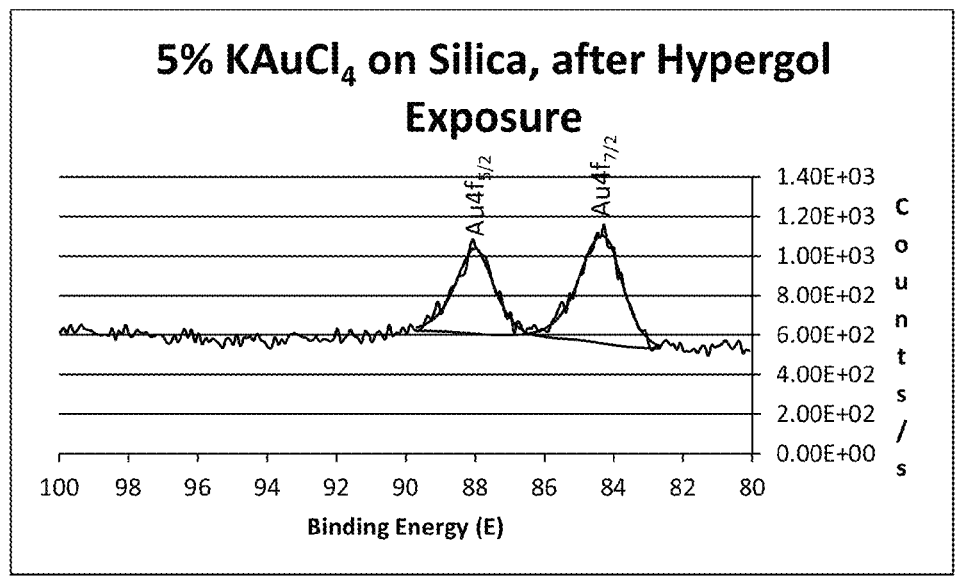

FIGS. 1A and 1B show representative XPS spectra for gold, KAuCl$_4$, 5% KAuCl$_4$ on silica, and 5% KAuCl$_4$ on silica exposed to hypergolic fuels. When comparing the unexposed and exposed 5% KAuCl$_4$ salt on silica spectra, clearly gold ions were being reduced to gold metal, since prior to hypergolic exposure, four peaks for binding energies were observes, whereas only two peaks for binding energies were observed after hypergolic exposure.

The atomic percentages of each element were measured prior to XPS analysis. The results are shown in Table 2. The atomic percentages were the average of three measurements, except for the large clump of gold on the exposed 5% KAuCl$_4$ on silica sample, which was a single measurement. The percentages of elements for bulk gold did not add to 100%, since the percentages of sulfur and nitrogen were not presented. Also, large amounts of carbonaceous contaminants were present on pure metallic samples as seen in the table.

TABLE 2

Measured atomic percentages of elements prior to XPS analysis.

| Sample | Atomic Oxygen % | Atomic Silicon % | Atomic Gold % | Atomic Carbon % | Binding Energy, eV, Au4f$_{7/2}$ for Au(0) |
|---|---|---|---|---|---|
| 1% KAuCl$_4$ on SiO$_2$ after exposure | 72.47 | 27.14 | 0.04 | 0.34 | 83.34 |
| 5% KAuCl$_4$ on SiO$_2$ after exposure | 72.44 | 26.83 | 0.16 | 0.54 | 83.70 |

TABLE 2-continued

Measured atomic percentages of elements prior to XPS analysis.

| Sample | Atomic Oxygen % | Atomic Silicon % | Atomic Gold % | Atomic Carbon % | Binding Energy, eV, Au4f$_{7/2}$ for Au(0) |
|---|---|---|---|---|---|
| 5% KAuCl$_4$ on SiO$_2$* after exposure | 66.68 | 24.95 | 5.77 | 2.59 | 83.97 |
| Bulk Gold | 16.04 | N/A | 20.32 | 59.75 | 84.00 |

*A large clump observed on the sample

A general trend was observed since the decrease in gold concentration tended to show a negative binding energy shift. The observed shift was opposite of other studies of gold on silica, which showed positive binding energy shifts, but the same as other reports that also showed negative shifts. Clearly, the data indicate that interactions of the reduced gold particles and the SiO$_2$ support were present that must affect the electronic characterization. As a side comment, a linear relationship correlated the inverse log of the shift in binding energy to the reciprocal of the atomic percentage of gold, see FIG. 2.

Figure 2:
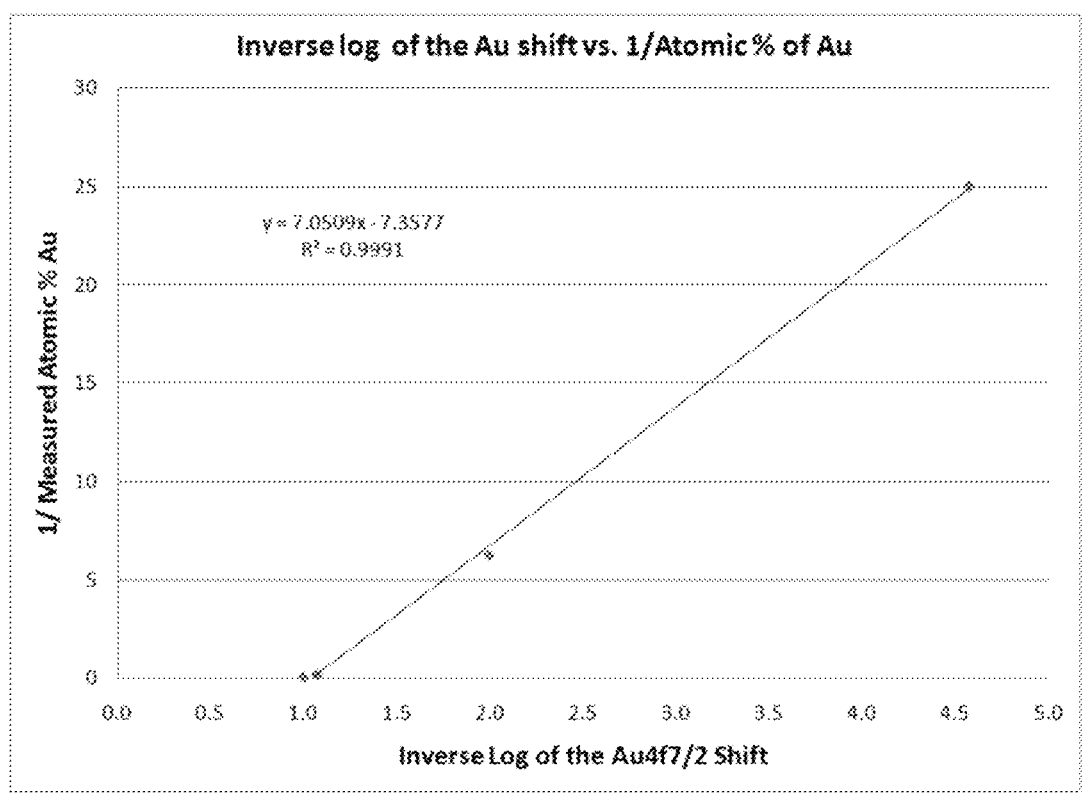
FIG. 2 is a graph showing the linear relationship of reciprocal of the atomic % of Au to the inverse log of the binding energy shift.
Figure 3:
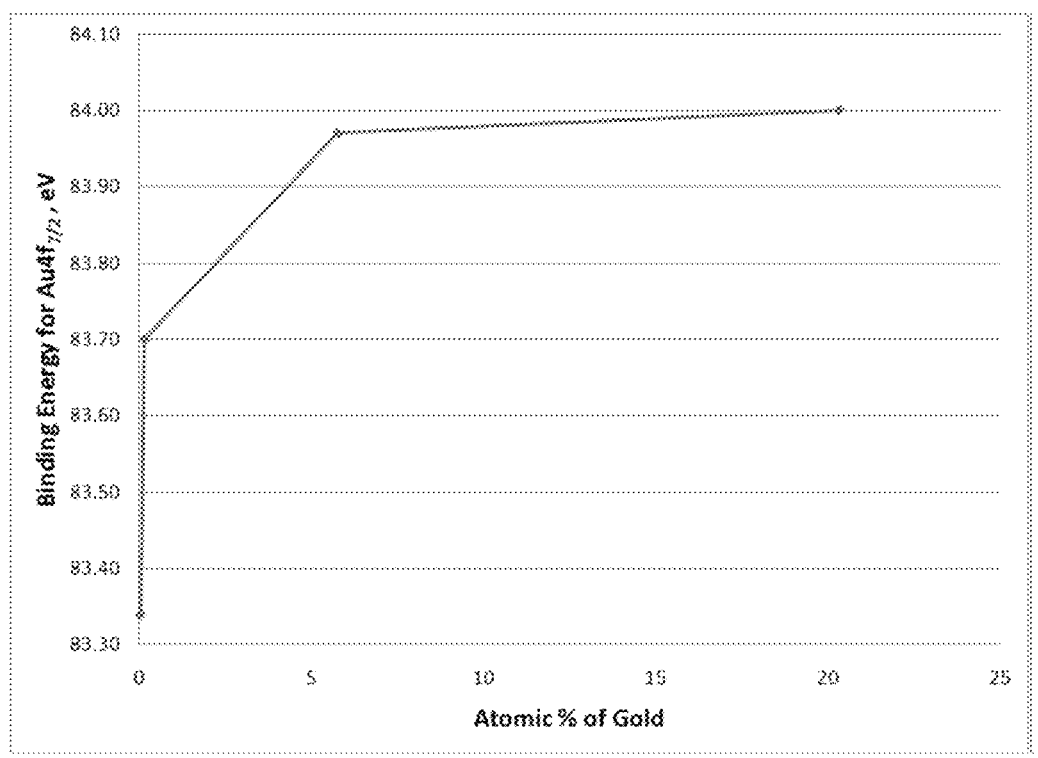
FIG. 3 is a graph of the binding energy of gold vs. the atomic % of gold.

FIG. 3 is a visual aid for explaining the linear relationship seen in FIG. 2. At very low concentrations of gold, the shift in binding energy increased more dramatically. However, when the concentration was closer to the bulk, the shift in binding energy was minimal. One reason for the increased shift in binding energy at lower concentrations has been attributed to an electron transfer from the support to the gold particle resulting in charging as well as the shape of the gold particles, since rounder gold particles had a more negative shift in binding energy.

XPS results showed that the KAuCl$_4$ salt contained gold in the +3 oxidative state. After exposure to hypergolic fuel, the gold was in its metallic form with a valence state of zero. A previous electrochemical study investigated the possible half reactions of hydrazine. If the conditions are not acidic, the following overall half reaction was proposed.

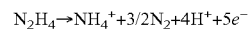

$$N_2H_4 \rightarrow NH_4^+ + 3/2N_2 + 4H^+ + 5e^-$$

Using the half reaction above, a possible balanced redox reaction with the gold salt when gold was in its 3+ oxidative state could be as follows.

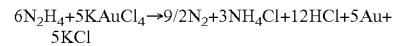

$$6N_2H_4 + 5KAuCl_4 \rightarrow 9/2N_2 + 3NH_4Cl + 12HCl + 5Au + 5KCl$$

Irreversible Hypergolic Sensing Tape

A hypergolic pigment-containing substrate including 1% KAuCl$_4$ salt on silica was incorporated into a TEFLON tape at a 3% load (also referred to herein as "hypertape"). The hypertape was exposed to 5,000 ppm hypergolic fuel at a flow rate of 2,000 sccm for 10 minutes. After 10 seconds of exposure, dark specs appeared on the hypertape. After 10 minutes, the dark specs on the hypertape appeared as it did after 10 seconds. The measured color difference was very low, ΔE=0.35, since the area of the color measured was approximately 1 cm$^2$. The light areas of the hypertape averaged in with the dark specs, resulting in a very low measured difference in color.

A second test using this batch of hypertape was conducted under similar conditions, however the concentration of hydrazine was much lower, approximately 40 ppm. The reactivity of the hypertape was very much the same, in that dark specs appeared very quickly, within approximately 20 seconds of exposure and very little change occurred over the next 10 minutes. These initial results seemed very promising for the hypertape, indicating that the hypergolic pigment was very responsive even when incorporated into a TEFLON matrix to the presence of hydrazine over a wide range of concentrations in a very short amount of time (i.e. less than a minute).

Currently, silicone is not an acceptable material for use with hydrazine. Studies showed that the silicone became brittle after 2 weeks exposure to hydrazine. The hypergolic pigment-containing substrate, which was 1% $KAuCl_4$ on silica, was incorporated into Dow Corning 739 thinned with Dow Corning OS-30 at a load of 5% and 10% by weight. The brittleness of the silicone was not an issue, since the ability of the hypertape to change to a uniform color was of interest. The hypertape was white when originally prepared, but changed to gray within 20 minutes from the reduction of the gold in the gold salt.

Dow Corning 739 contains calcium carbonate and magnesium carbonate to aid in the products flame resistance. To determine if additives were causing the premature graying of the hypertape, the hypergolic pigment-containing substrate was incorporated into Dow Corning 3145 at a 5% (w/w) load, which was not flame resistant. The hypertape was yellow in color and remained yellow. The hypertape was exposed to 800 ppm hypergolic fuel flowing at 100 sccm. The hypertape changed to a light gray color within 20 minutes of exposure. The hypertape was exposed to the hypergolic fuel for 1 hour. Upon removal, the hypertape appeared a medium shade of gray. However, after two days passed, the hypertape appeared much darker. The ΔE comparing the exposed hypertape to the unexposed hypertape was 43.

The embodiments of the present invention were described in sufficient detail to enable those of ordinary skill in the art to practice the invention, and it is to be understood that other embodiments may be utilized and that changes may be made without departing from the scope of the present invention. The following detailed description is, therefore, not to be taken in a limiting sense, and the scope of the present invention is defined only by the claims and equivalents thereof.

What is claimed is:

1. A chemochromic indicator for detecting the presence of a hypergolic fuel comprising
   a) an inert spherical particle substrate having a particle size diameter of 50-200 microns and
   b) a hypergolic fuel sensing chemochromic pigment plated onto said inert spherical particle substrate, wherein said hypergolic fuel sensing chemochromic pigment is capable of an oxidation-reduction reaction with hypergolic fuels and undergoes an irreversible color change from a first color to a second color when undergoing an oxidation-reduction reaction with hypergolic fuels.

2. The chemochromic indicator of claim 1 wherein said hypergolic fuel sensing chemochromic pigment comprises potassium tetrachloroaurate ($KAuCl_4$), potassium permanganate ($KMnO_4$), or mixtures thereof.

3. The chemochromic indicator of claim 1 wherein said inert spherical particle substrate is a ceramic oxide.

4. The chemochromic indicator of claim 3 wherein said ceramic oxide is selected from the group consisting of titanium dioxide, silica, alumina, zirconium oxide, and mixtures thereof.

5. The chemochromic indicator of claim 1, wherein said hypergolic fuel is hydrazine or a hydrazine derivative.

6. A method for detecting the presence of a hypergolic fuel comprising exposing said chemochromic indicator of claim 1 to a hypergolic fuel such that said hypergolic fuel sensing chemochromic pigment changes from a first color to a second color when said hypergolic fuel sensing chemochromic pigment undergoes an oxidation-reduction reaction in the presence of said hypergolic fuel thereby indicating the presence of the hypergolic fuel.

7. The method of claim 6, wherein said hypergolic fuel is hydrazine or derivatives of hydrazine.

8. An article capable of sensing the presence of hypergolic fuels comprising
   (a) a chemochromic indicator for detecting the presence of a hypergolic fuel comprising
      i) an inert spherical particle substrate and
      ii) a hypergolic fuel sensing chemochromic pigment plated onto said inert substrate, wherein said hypergolic fuel sensing chemochromic pigment is capable of an oxidation-reduction reaction with hypergolic fuels and undergoes an irreversible color change from a first color to a second color when undergoing an oxidation-reduction reaction with hypergolic fuels; and
   (b) a host material selected from the group consisting of a wipe material, a silicone tape, a polytetrafluoroethylene tape, a manufactured polymer part, a textile fiber or fabric, an extruded polymer part, and a paint.

9. The article of claim 8 wherein said indicator is deposited onto the host material.

10. The article of claim 8 where said indicator is incorporated into the host material through processing methods consisting of mixing, melt mixing, extrusion, and molding.

11. The article of claim 8, further comprising an anti-static coating applied to a surface of the article.

12. The article of claim 8, further comprising a UV protectant applied to a surface of the article.

* * * * *